(12) United States Patent  
Stawiaski et al.

(10) Patent No.: US 11,045,259 B2  
(45) Date of Patent: Jun. 29, 2021

(54) SURGICAL NAVIGATION SYSTEM

(71) Applicant: Stryker European Holdings I, LLC, Kalamazoo, MI (US)

(72) Inventors: Jean Stawiaski, Kirchzarten (DE); Fadi Ghanam, Schallstadt (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 45 days.

(21) Appl. No.: 16/434,849

(22) Filed: Jun. 7, 2019

(65) Prior Publication Data

US 2019/0374289 A1 Dec. 12, 2019

(30) Foreign Application Priority Data

Jun. 8, 2018 (EP) .................................... 18176829

(51) Int. Cl.
*G06T 3/00* (2006.01)
*A61B 34/20* (2016.01)
*A61B 90/00* (2016.01)

(52) U.S. Cl.
CPC ............ *A61B 34/20* (2016.02); *A61B 90/361* (2016.02); *A61B 2034/2051* (2016.02);
(Continued)

(58) Field of Classification Search
CPC ................. A61B 34/20; A61B 90/361; A61B 2034/2051; A61B 2034/2057;
(Continued)

(56) References Cited

U.S. PATENT DOCUMENTS 7,289,211 B1 * 10/2007 Walsh, Jr. ............ A61B 5/0086  
356/369  
7,588,535 B2 * 9/2009 Adler ................. A61B 1/00009  
600/109  
(Continued)

FOREIGN PATENT DOCUMENTS

DE 102010042278 A1 4/2012  
EP 1862115 A1 12/2007  
(Continued)

OTHER PUBLICATIONS

Atkinson, Gary A., "Recovery of Surface Orientation From Diffuse Polarization", IEEE Transactions on Image Processing, vol. 15, No. 6, Jun. 2006, pp. 1653-1664.  
(Continued)

*Primary Examiner* — Gregory M Desire  
(74) *Attorney, Agent, or Firm* — Howard & Howard Attorneys PLLC

(57) ABSTRACT

A surgical navigation system is provided. The surgical navigation system comprises a camera system comprising at least one camera. The camera system is capable of capturing images of light that is filtered through at least three different polarization angles. The surgical navigation system further comprises a processor having access to three dimensional image data of a surgical object. The processor is configured to determine first surface normals from the three dimensional image data of the surgical object. The processor is further configured to determine second surface normals from at least three images captured by the camera system of the surgical object under different polarization angles. The processor is configured to align the first surface normals with the second surface normals. Furthermore, a method for operating a surgical navigation system is provided.

20 Claims, 7 Drawing Sheets

(52) U.S. Cl.
CPC .......... *A61B 2034/2057* (2016.02); *A61B 2034/2063* (2016.02); *A61B 2034/2068* (2016.02); *A61B 2034/2072* (2016.02); *A61B 2090/364* (2016.02)

(58) Field of Classification Search
CPC .... A61B 2034/2063; A61B 2034/2068; A61B 2034/2072; A61B 2090/364
See application file for complete search history.

(56) References Cited

U.S. PATENT DOCUMENTS

| | | | | |
|---|---|---|---|---|
| 8,731,250 | B2 * | 5/2014 | Martin | G06K 9/00033 382/124 |
| 8,760,517 | B2 * | 6/2014 | Sarwar | G06T 7/596 348/156 |
| 8,948,851 | B2 * | 2/2015 | Leblond | A61B 5/416 600/476 |
| 9,464,938 | B2 * | 10/2016 | Tillotson | G01J 3/0224 |
| 9,901,409 | B2 * | 2/2018 | Yang | A61B 34/20 |
| 10,178,955 | B2 * | 1/2019 | Rucker | A61B 5/0036 |
| 10,285,761 | B2 * | 5/2019 | Piron | A61B 34/00 |
| 10,478,253 | B2 * | 11/2019 | Mak | A61B 90/37 |
| 10,708,557 | B1 * | 7/2020 | Briggs | H04N 13/239 |
| 2007/0280423 | A1 | 12/2007 | Schmidt | |
| 2015/0287236 | A1 | 10/2015 | Winne et al. | |
| 2016/0261844 | A1 | 9/2016 | Kadambi et al. | |

FOREIGN PATENT DOCUMENTS

| | | |
|---|---|---|
| EP | 2202688 A2 | 6/2010 |
| WO | 2007033379 A2 | 3/2007 |
| WO | 2014068106 A1 | 5/2014 |
| WO | 2016127173 A1 | 8/2016 |

OTHER PUBLICATIONS

Machine-Assisted English language abstract and machine-assisted English translation for DE 10 2010 042 278 extracted from espacenet.com database on Jul. 10, 2019, 19 pages.

English language abstract for EP 1 862 115 extracted from espacenet.com database on Jul. 10, 2019, 1 page.

English language abstract for WO 2014/068106 extracted from espacenet.com database on Jul. 10, 2019, 2 pages.

* cited by examiner

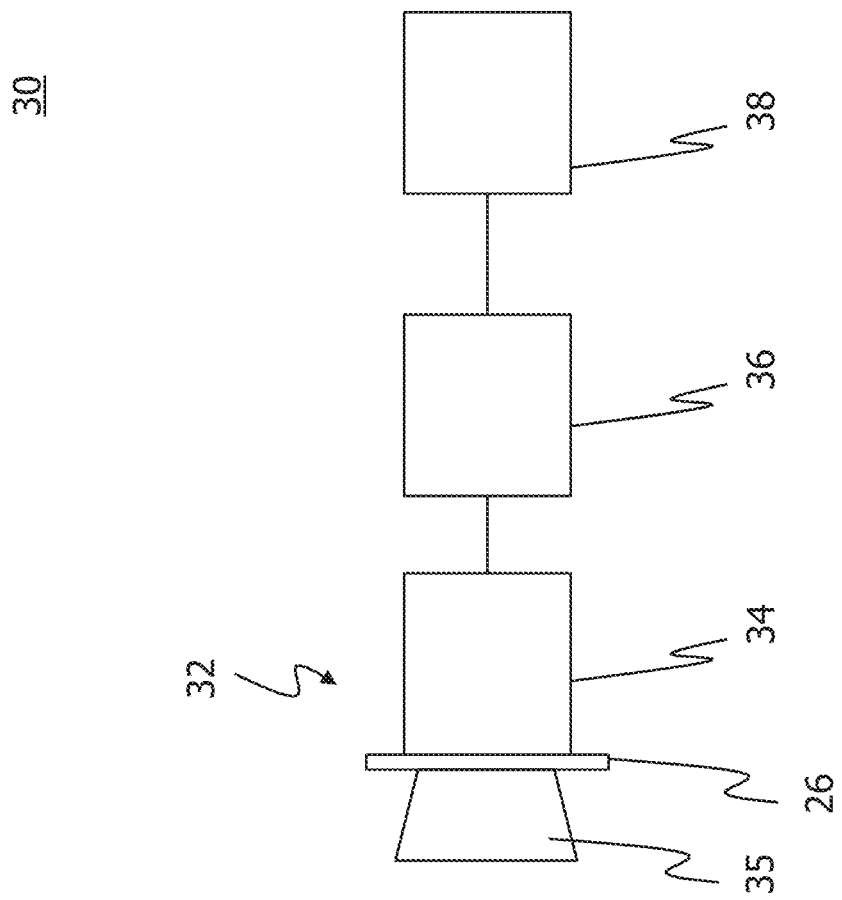
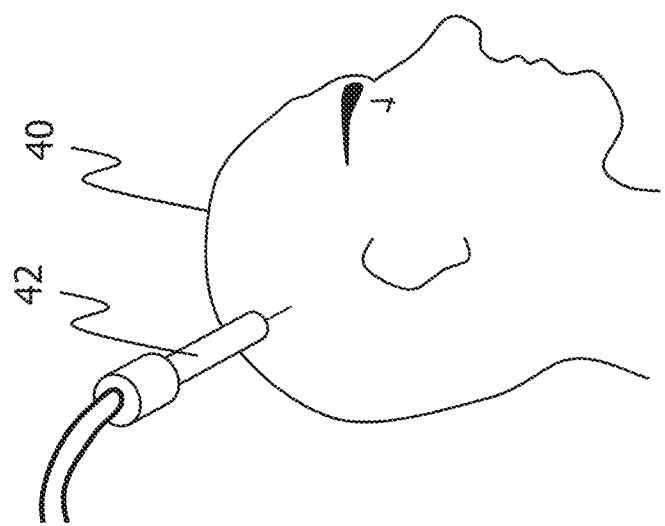
Fig. 3

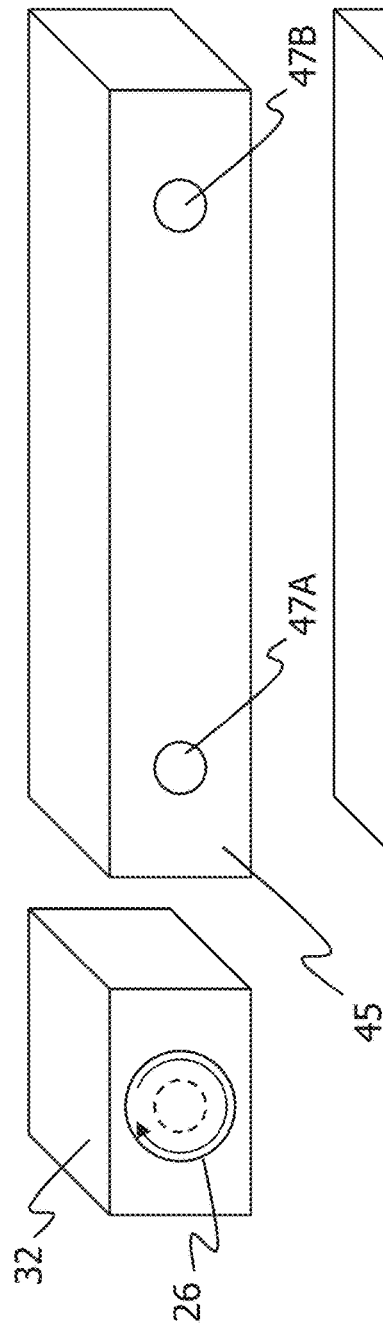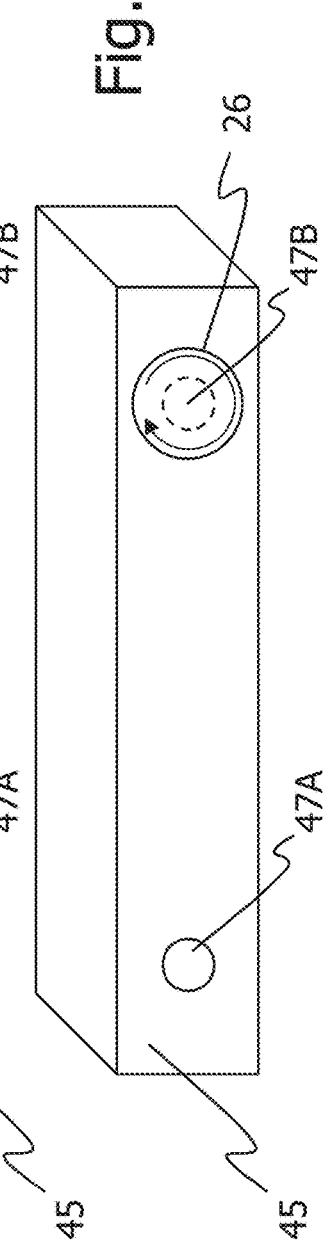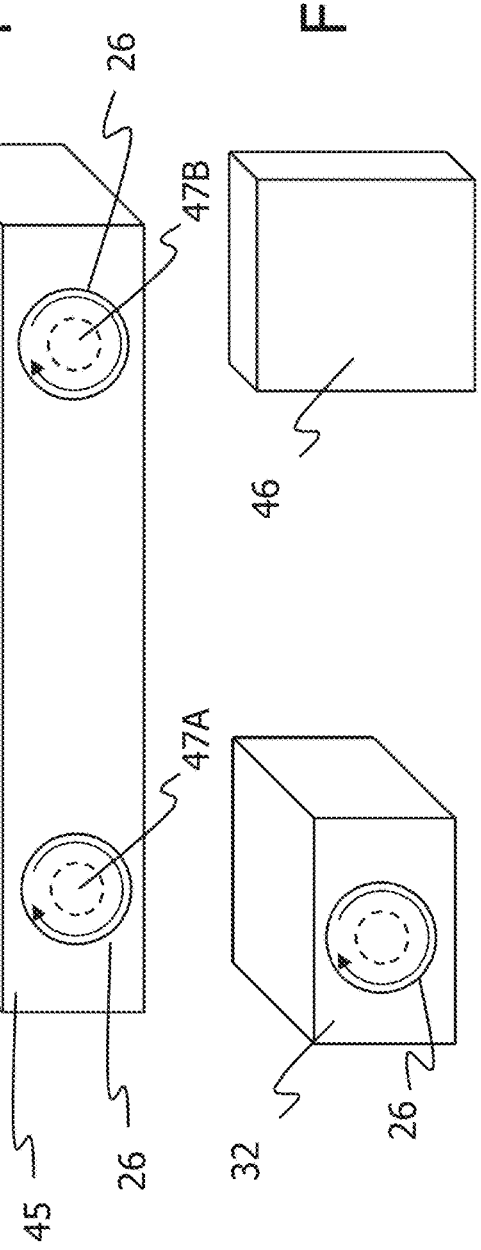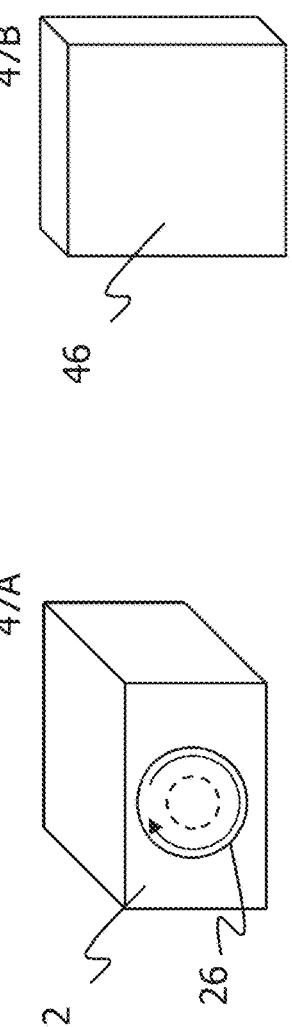

SURGICAL NAVIGATION SYSTEM

RELATED APPLICATIONS

This application claims priority to European Patent Application No. 18 176 829.2, filed Jun. 8, 2018, the content of which is incorporated herein by reference in its entirety.

TECHNICAL FIELD

The present disclosure generally relates to a surgical navigation system. In particular, a surgical navigation system comprising a camera capable of capturing images filtered through different polarization angles is presented.

BACKGROUND

During surgery, a surgeon typically inserts an instrument into the body of a patient. Once inside the patient's body, the surgeon loses vision of the tip of the instrument. In order to help the surgeon navigate the instrument in such a case, a surgical navigation system can be used that tracks the position and/or orientation of the instrument relative to the patient and provides visual or acoustic guidance to the surgeon. One way to achieve this is to calculate a position of a virtual instrument (e.g., a CAD data set of the instrument) relative to a virtual patient (e.g., a CT scan of the patient) and to display on a monitor where the calculated position of the virtual instrument tip is located relative to the virtual patient.

Navigation in regard to surgical objects, such as the patient or a surgical instrument, typically comprises two procedures: registration and tracking. During registration, a spatial relationship between different coordinate systems (e.g., of the patient in an operating room and a previously acquired CT scan of the patient) is determined. This is commonly achieved by determining a transformation between the associated coordinate systems. After successful registration, a surgical object can be tracked, wherein changes of the position and/or orientation of the surgical object are determined (e.g., via a camera in the operating room) in one coordinate system and transformed into the other coordinate system.

It has recently been proposed to utilize surface-from-polarization, SFP, techniques for surgical applications. Such SFP techniques comprise a capturing of images under different polarization angles and a reconstruction of surface normals from these captured images. Prior art in this regard is known from US 2016/0261844 A1 which discloses capturing a first and a second set of images, wherein polarization surface normals are calculated based on the second set of images. A first depth map is calculated based on the first set of images and a second depth map is calculated based on the first depth map and polarization surface normals. This means that in order to calculate the second depth map, a first depth map needs to be acquired.

SUMMARY

There is a need for a surgical navigation system that improves the registration and/or tracking for a surgical object.

According to one aspect, a surgical navigation system is provided. The surgical navigation system comprises a camera system comprising at least one camera, wherein the camera system is capable of capturing images of light that is filtered through at least three different polarization angles. The surgical navigation system further comprises a processor having access to three dimensional image data of a surgical object. The processor is configured to determine first surface normals from the three dimensional image data of the surgical object. The processor is further configured to determine second surface normals of the surgical object from at least three images captured of the surgical object by the camera system under different polarization angles. The processor is also configured to align the first surface normals with the second surface normals.

The camera system may comprise a single camera. The camera system may alternatively comprise a plurality of cameras. The plurality of cameras may be spatially spaced apart.

The light for the captured images may be filtered through an adjustable or non-adjustable polarizing filter. The camera system may comprise a plurality of cameras each with a polarizing filter, wherein the polarizing filters have different polarization angles relative to each other. The camera system may comprise optically active elements, such as liquid crystal cells. The optically active elements may be configured to rotate a polarization angle of polarized light entering the camera system. The optically active elements may be electrically operable.

The surgical object may be a patient or a part thereof or a surgical instrument. The three dimensional image data of the patient may be acquired by computed tomography, CT, magnetic resonance imaging, MRI, positron emission tomography, PET, ultrasound or other scanning procedures that acquires three dimensional patient data. The three dimensional data of the surgical instrument may be acquired in the form of a CAD data set, a three dimensional laser scan or dimensional parameters that were entered by the user.

The processor may be configured to align the second surface normals with the first surface normals to determine a transformation of coordinates of the first surface normals in a first coordinate system into a second coordinate system of the second surface normals. The processor may be configured to align the second surface normals with the first surface normals to determine an inverse transformation of coordinates of the second surface normals in a second coordinate system into a first coordinate system of the first surface normals. The transformation and/or inverse transformation may be determined by a minimization of a sum of differences between the first surface normals and the second surface normals. The transformation may also be determined by a minimization of a sum of differences between projections of the first surface normals and the second surface normals onto an image plane of the camera system. A difference may be calculated as the magnitude of a vector difference between two surface normals.

The processor may be configured to differentiate if the surgical object is of a first type or a second type based on a degree of polarization determined for the second surface normals of the surgical object. The processor may be configured to determine that the surgical object is of the first type if a degree of polarization determined for the second surface normals of the surgical object is lower than a first threshold. Additionally, or in the alternative, the processor may be configured to determine that the surgical object is of the second type if a degree of polarization determined for the second surface normals of the surgical object is higher than a second threshold. The first type surgical object may be a patient and the second type surgical object may be a surgical instrument. The first threshold may be identical to the second threshold.

The processor may be configured to differentiate if a second surface normal of the second surface normals is pertaining to a surface or surface region covered by liquid based on a degree of polarization determined for the second surface normal of the second surface normals. The processor may be configured to determine that the second surface normal of the second surface normals is pertaining to a surface or surface region covered by liquid if the degree of polarization determined for the second surface normal of the second surface normals is above a third threshold. The surface covering liquid may comprise at least one of blood, water, disinfectant and pus.

The processor may be configured to differentiate if a second surface normal of the second surface normals is pertaining to a surface emitting or reflecting light based on a degree of polarization determined for the second surface normal of the second surface normals. The processor may be configured to identify that the second surface normal of the second surface normals is pertaining to a light emitting surface if the degree of polarization determined for the second surface normal of the second normals is below a fourth threshold. The processor may be configured to identify that the second surface normal of the second surface normals is pertaining to a light reflecting surface if the degree of polarization determined for the second surface normal of the second normals is above a fifth threshold. The fourth threshold may be identical to the fifth threshold.

The processor may be configured to determine the second surface normals from the at least three images by fitting a light intensity of pixels of the captured images to a sinusoid model that describes a magnitude of a light beam having a light beam polarization angle passing through a polarization filter. The processor may be configured to determine the light polarization angle and a degree of polarization from the fitted light intensity.

The processor may be configured to determine the second surface normals from the at least three images by using a Fresnel equation. A dielectric constant used in the Fresnel equation may be set to a value between 1.3 and 1.6.

The processor may be configured to determine or have access to at least one parameter of at least one camera of the camera system that is indicative of at least one of a spatial position and optical properties of the at least one camera of the camera system. The processor may be configured to determine or have access to at least one parameter of each of multiple cameras of the camera system. The at least one parameter may be indicative of a position and/or orientation of the at least one camera relative to the surgical object and/or another camera. The at least one parameter may be indicative of at least one of a distortion, a focal length, a lens arrangement and a sensor position relative to the lens arrangement.

The processor may be further configured to track a second type surgical object relative to a first type surgical object by calculating a position and orientation of the second type surgical object relative to the first type surgical object. The processor may be configured to track the second type surgical object and the first type surgical object relative to a camera coordinate system by calculating a position and orientation of the second type surgical object and the first type surgical object relative to the camera coordinate system. The first type surgical object may be a patient and the second type surgical object may be a surgical instrument.

The three dimensional image data may be previously acquired from an unknown position and/or viewing angle. For example, the position and/or viewing angle of an imaging device that has acquired the three dimensional image data may be unknown. Specifically, a relationship (e.g., the transformation parameters) between the viewing angle of the imaging device and the viewing angle of the camera system may be unknown.

According to a second aspect, a method for operating a surgical navigation system is provided. The surgical navigation system comprises a camera system comprising at least one camera, wherein the camera system is capable of capturing images of light that is filtered through at least three different polarization angles. The processor further has access to three dimensional image data of a surgical object. The method comprises determining first surface normals of the surgical object from the three dimensional image data. The method further comprises determining second surface normals of the surgical object from at least three images of the surgical object captured by the camera system under different polarization angles. The method comprises aligning the first surface normals with the second surface normals.

According to a third aspect, a non-transitory computer-readable medium that stores programming instructions for execution, that when executed on at least one processor, cause the at least one processor to carry out the method explained above.

BRIEF DESCRIPTION OF THE DRAWINGS

Further details, advantages and aspects of the present disclosure will become apparent from the following embodiments taken in conjunction with the drawings, wherein:

FIG. 3 shows an embodiment of a surgical navigation system comprising a camera system with one camera;

FIG. 7A shows an embodiment of a surgical navigation system with a rotatable polarizing filter in combination with a stereo camera;

FIG. 7B shows an embodiment of a stereo camera, wherein one of the two cameras comprises a rotatable polarizing filter;

FIG. 7C shows an embodiment of a stereo camera, wherein both cameras comprise a rotatable polarizing filter; and FIG. 7D shows an embodiment of an apparatus for electromagnetic tracking in combination with a surgical navigation system.

DETAILED DESCRIPTION

Figure 1:
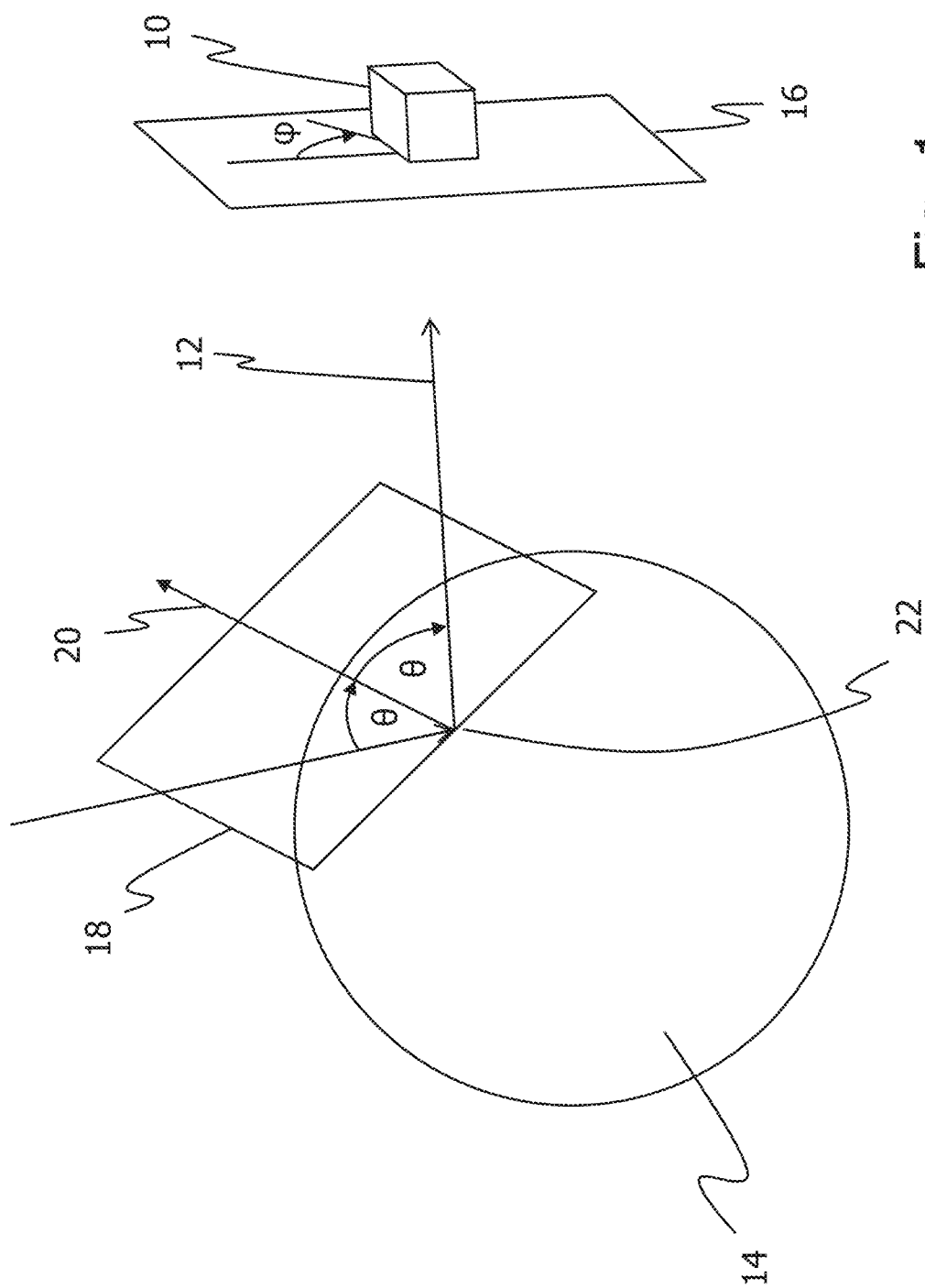
FIG. 1 shows a light sensor detecting a light beam that was reflected off the surface of an object.

In the following description, exemplary embodiments of a surgical navigation system and a method for operating a surgical navigation system will be explained with reference to the drawings. The same or similar reference numerals will be used to denote the same or similar structural features.

The embodiments described below incorporate a technique commonly referred to as "Surface-From-Polarization", or SFP. Before describing the embodiments in greater detail, the physical background of SFP is described first.

With reference to FIG. 1 it will be explained how a light beam reflecting of a surface is polarized and in what way the surface normal at the point of incidence is correlated to the polarization of the light beam. Using an exemplary setup with a light sensor shown in FIG. 2, it will then be explained how to gather information from the reflected light beam that allows determining the surface normal. The principle is then expanded to a plurality of light sensors in the form of a pixel array, which allows generating a surface normal map.

FIG. 1 shows a light sensor 10 detecting a light beam 12 that was reflected off the surface of an object 14. The light sensor 10 may belong to any of the cameras or camera systems discussed in more detail below. The exemplary object shown in FIG. 1 is a sphere. The object 14 may be any other object with a surface, in particular a surgical object such as a patient or a surgical instrument. The surface normals of the object 14 are to be determined to allow registering and tracking of the surface.

When the light beam 12 is reflected off the surface, the path of the light beam 12 is arranged in an incidence plane 18 that comprises a surface normal 20 at a point of incidence 22 of the light beam 12. The incident and reflection angles θ of the light beam 12 are equal and formed between the light beam 12 and the surface normal 20 with the point of incidence 22 forming the vortex. The light sensor 10 has an (imaginary) image plane 16. The reflected light beam 12 is essentially perpendicularly oriented relative to the image plane 16. Since the reflected light beam 12 extends perpendicular to the image plane 16 of the light sensor 10, the reflection angle θ also defines a zenith angle θ relative to the light sensor 10. Therefore, when determining the orientation of the surface normal 20, one part of the orientation of the surface normal 20 may be determined by calculating the azimuth angle θ.

The other part of the orientation of the surface normal 20 is determined by an azimuth angle φ. The azimuth angle φ of the surface normal 20 is correlated with the polarization of the light beam 12. A reflected light beam is at least partially polarized in a direction perpendicular to the plane of incidence 18 and therefore also the surface normal 20. Consequently, the angle of polarization φ is also the azimuth angle φ of the surface normal 20 relative to the light sensor 10.

In the following, it will be explained how the azimuth angle φ and the zenith angle θ can be determined from detecting reflected light under different polarization angles of a polarizing filter.

Figure 2:
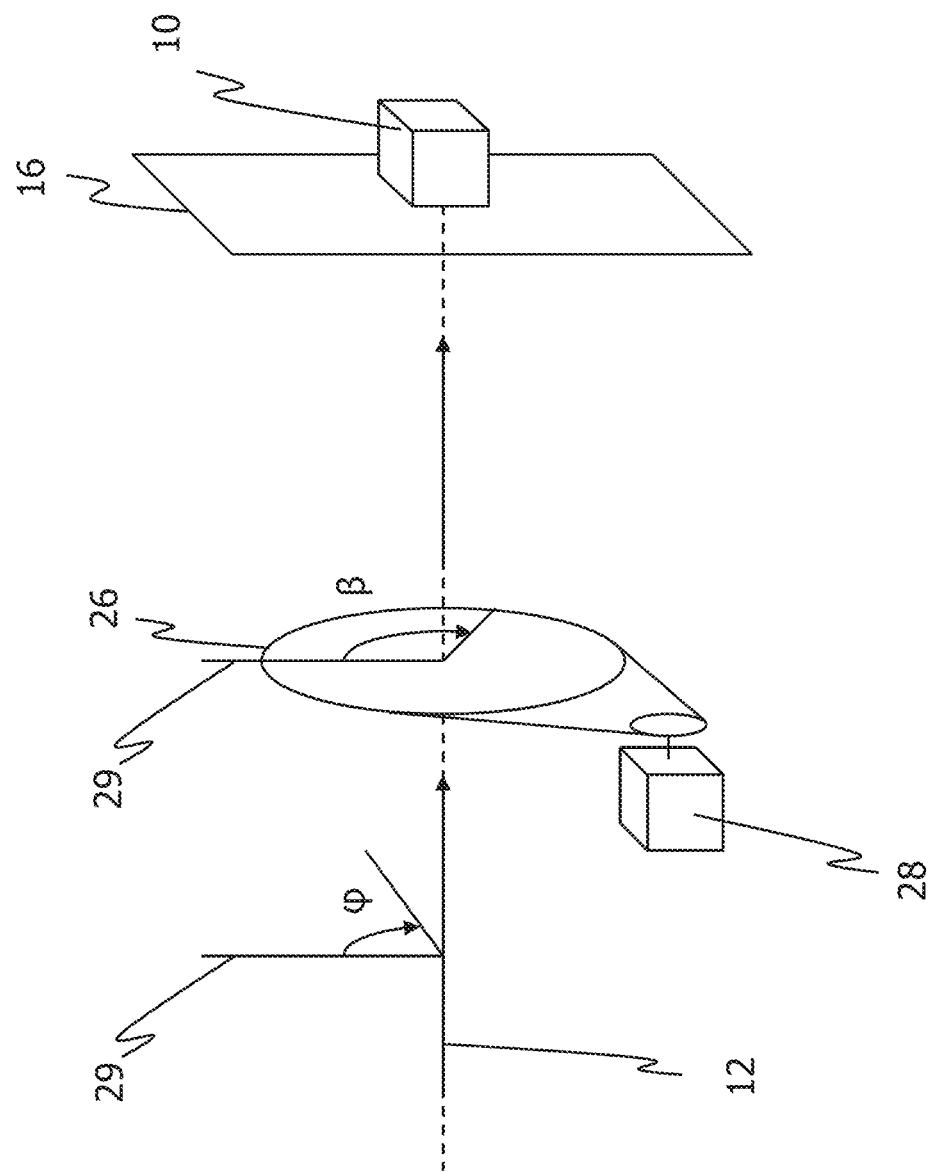
FIG. 2 shows a light sensor detecting the intensity of a polarized or partially polarized light beam after passing through a polarization filter.

FIG. 2 shows the light sensor 10 detecting the intensity of the polarized or partially polarized light beam 12 after passing through a polarization filter 26. The polarization filter 26 is oriented essentially in parallel to the image plane 16. The polarization filter 26 is rotatable, e.g., by means of a motor 28, wherein a polarization filter angle β relative to a reference axis 29, which in FIG. 1 is a vertical axis, can be adjusted by a rotation of the polarization filter 26.

The light beam 12 in FIG. 2 is essentially perpendicularly oriented relative to the polarization filter 26 and the image plane 16. Furthermore, the light beam 12 has a light beam polarization angle φ between the reference axis 29 and the polarization angle of the light beam 12.

When the polarization of the light beam 12 and the polarization filter 26 align (i.e. β≈φ), the light sensor 10 senses a maximum light intensity $I_{max}$. If the initial light beam 12 is (completely) polarized, the light beam 12 then passes the polarization filter 26 essentially unattenuated. If the initial light beam 12 is only partially polarized, the attenuation of the polarization filter 26 is minimized when β=φ.

In the case the polarization of the light beam 12 and the polarization filter 26 are aligned perpendicular to each other (i.e. β≈φ±90°, the light sensor 10 senses a minimum intensity $I_{min}$.

While rotating the polarization filter 26, the light sensor 12 detects a light intensity that falls between $I_{min}$ and $I_{max}$, wherein the detected intensity I(β, φ) can be described by equation (1):

$$I(\beta, \varphi) = \frac{I_{max} + I_{min}}{2} + \frac{I_{max} - I_{min}}{2} \cdot \cos(2\beta - 2\varphi) \quad \text{(Eq. 1)}$$

Equation (1) has three parameters: The maximum light intensity $I_{max}$, the minimum light intensity $I_{min}$ and the light beam polarization angle φ. In order to identify these three parameters, the light intensity is measured for three different polarization filter angles $\beta_1$, $\beta_2$ and $\beta_3$. The three polarization angles may for example be $\beta_1=0°$, $\beta_2=45°$ and $\beta_3=90°$. Under these three polarization angles, the light sensor detects three different intensities $I_1$, $I_2$ and $I_3$. The light beam polarization angle φ can be determined using equation (2) which is based on equation (1):

$$\varphi = \frac{1}{2}\arctan\left(\frac{I_1 + I_3 - 2I_2}{I_3 - I_1}\right) + 90°, \text{ if } I_3 < I_1 \text{ or } I_2 < I_1 \text{ or} \quad \text{(Eq. 2)}$$

$$\varphi = \frac{1}{2}\arctan\left(\frac{I_1 + I_3 - 2I_2}{I_3 - I_1}\right) - 90°, \text{ for any other case.}$$

Therefore, by sensing the intensity of the light beam 12 and applying equation (2) to the obtained intensity values, one can calculate the light beam polarization angle φ, which is also, as explained above, the azimuth angle φ of the surface normal 20 (see FIG. 1). It should be noted that equation (1) has the same solution for φ as well as φ±π. Consequently, the azimuth angle φ calculated by equation (2) has a 180-degree angle ambiguity. This issue will be addressed further below.

The other angle that needs to be determined is the zenith angle θ. For this purpose, the following equation (3) is used, which describes the degree of polarization ρ:

$$\rho = \frac{I_3 - I_1}{(I_3 + I_1) \cdot \cos 2\phi} \quad \text{(Eq. 3)}$$

Substituting the Fresnel Equations into equation (3) yields the following equation (4) for the polarization ρ:

$$\rho = \frac{\left(n - \frac{1}{n}\right)^2 \sin^2\theta}{2 + 2n^2 - \left(n + \frac{1}{n}\right)^2 \sin^2\theta + 4\cos\theta\sqrt{n^2 - \sin^2\theta}}, \quad \text{(Eq. 4)}$$

wherein n denotes the refractive index and θ the zenith angle. The refractive index n is usually not known. However, for most dielectrics the refractive index can be set to a value between 1.3 and 1.6. With a set refractive index n (e.g., 1.4) and the degree of polarization known from equation (3), the zenith angle θ can be estimated from equation (4) (e.g., in closed-form or through numerical optimization).

Equation (4) may be applied for diffusive reflection. In the case of specular reflection, equation (5) may be used $$\rho_{sepc} = \frac{2n\tan\theta\sin\theta}{\tan^2\theta\sin^2\theta + |n^*|^2}, \quad (Eq. 5)$$

with $|n^*|^2 = n^2(t+\kappa^2)$, wherein κ is the attenuation index of the material and the degree of specular polarization is $\rho_{spec}$.

With the azimuth angle φ and the zenith angle θ of the surface normal 20 calculated via the above equations (1) to (5), a vector $\vec{p}$ of the surface normal 20 can be calculated by the following equation (6):

$$\vec{p} = \begin{pmatrix} p_x \\ p_y \\ p_z \end{pmatrix} = \begin{pmatrix} \cos\alpha & \cos\theta \\ \sin\alpha & \sin\theta \\ & \cos\theta \end{pmatrix} \quad (Eq. 6)$$

with α=φ or φ+π.

The above equations allow calculating the vector of a surface normal relative to a single light sensor 10. Therefore, one light sensor 10 may be assigned one surface normal 20. By employing a camera with an array of light sensors 10, a plurality of corresponding surface normals may be determined. Such an array of light sensors may be provided by a digital camera in form of a charge-couple device, complementary metal-oxide-semiconductor or other image sensor with an array of light sensors that allow recording a plurality of pixels.

FIG. 3 shows an embodiment of a surgical navigation system 30 comprising a camera system 32 with one camera 34. The camera 34 comprises a pixel array (e.g., a CCD array) that essentially comprises a plurality of light sensors 10 as discussed above. The camera system 32 further comprises a rotatable polarization filter 26 which is configured to polarize light entering an objective 35 of the camera 34. By adjusting the polarization angle of the polarization filter 26, the polarization angle of light entering the camera 34 can be adjusted.

The surgical navigation system 30 further comprises a processor 36 that is configured to receive image data of the camera system 32. The processor 36 may receive the image data via a cable, wireless data transfer or an external storage medium that receives the image data from the camera system 32.

The processor 36 is configured to control the polarization angle of the polarization filter 26. Alternatively, the camera system 32 or the camera 34 may be configured to control the polarization angle of the polarization filter 26. In such a case, the camera system 32 or camera 34 captures images under different polarization angles and sends the image data to the processor 36 together with information that indicates under which polarization angle the images were captured.

The surgical navigation system 30 further comprises a storage medium 38. The storage medium 38 stores three dimensional image data of one or more surgical objects. The surgical objects may comprise a patient 40 and a surgical instrument 42. Three dimensional image data of the patient 40 may have been acquired by computed tomography, CT, magnetic resonance imaging, MRI, positron emission tomography, PET, ultrasound or other scanning procedures that acquire three dimensional data of the patient 40. The three dimensional data of the surgical instrument 42 may be acquired in form of CAD data, a three dimensional laser scan or dimensional parameters that were entered by the user. FIG. 3 shows a single storage medium 38 that is configured to store three dimensional image data for a plurality of surgical objects, such as three dimensional image data of the patient 40 and of the surgical instrument 42. Alternatively, a plurality of storage media may be provided, wherein three dimensional image data for different surgical objects is stored on different storage media.

Figure 4:
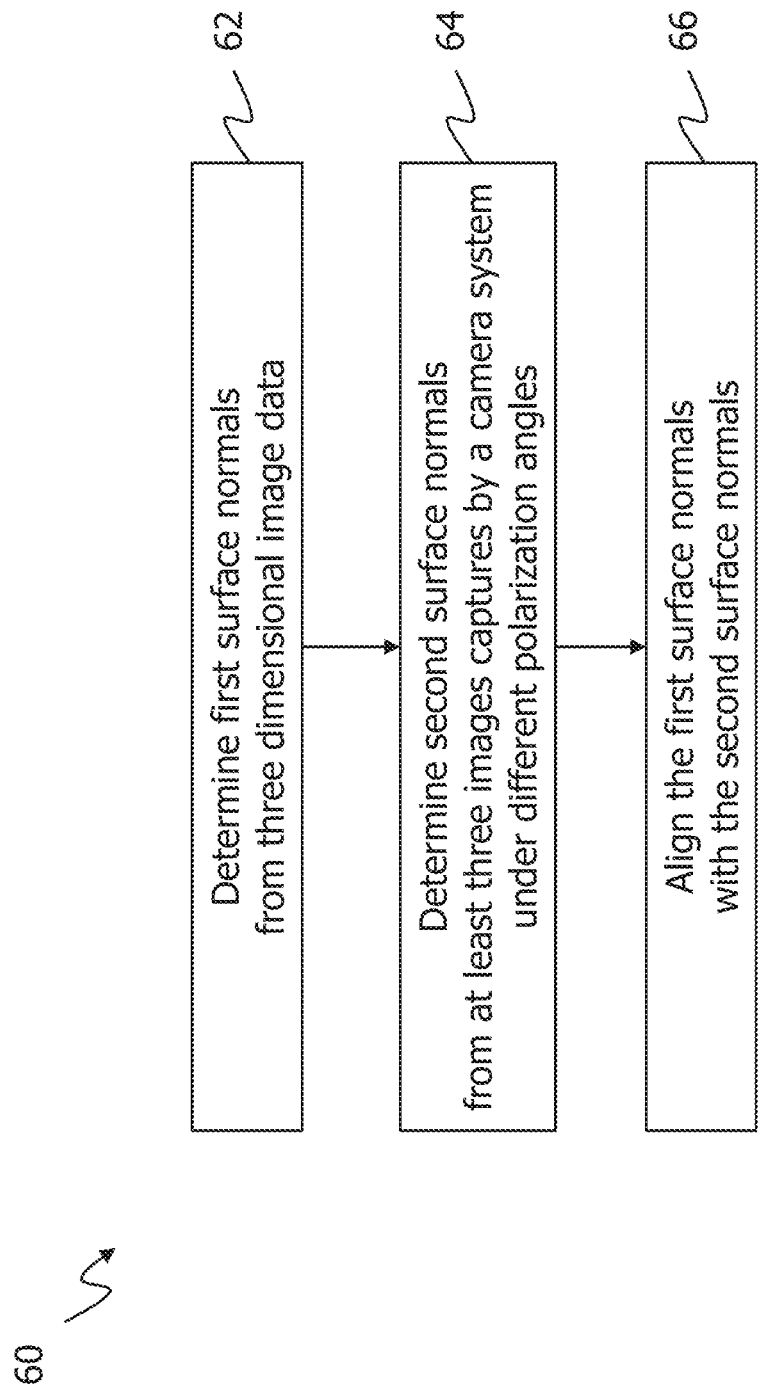
FIG. 4 shows a flow diagram of a method embodiment of operating a surgical navigation system.

FIG. 4 shows a flow diagram of a method embodiment 60 of operating the surgical navigation system 30 of FIG. 3 or another surgical navigation system.

The method 60 comprises a step 62 of determining first surface normals from the three dimensional image data. The processor 36 determines, for example, a surface of the surgical object from analysing a density gradient of the three dimensional image data (e.g., of a CT scan) or by determining outer polygons of a three dimensional model of the surgical object. The processor 36 then reconstructs the first surface normals by comparing the position of the corresponding area of the surface with a surrounding area of the surface. From these positions a smooth surface may be interpolated from which the first surface normals can be calculated. The first surface normals are assigned three-dimensional coordinates of corresponding surface positions in a first coordinate system.

According to step 64, second surface normals 20 are determined from at least three images captured by the camera system 32 under different polarization angles, wherein the at least three images are captures of the surgical object 40, 42. To this end, the camera 34 shown in FIG. 3 is configured to record three images of at least one of the patient 40 and the surgical instrument 42 under different polarization angles of the polarization filter 26. For each pixel of the camera 34, three different light intensities are recorded, respectively. According to the equations described above, for each pixel a second surface normal $\vec{p}$ is calculated. These second surface normals $\vec{p}$ form a polarization normal map PN, wherein each pixel of the two-dimensional pixel array is assigned a three-component normal vector $\vec{p}$:

$$PN: Z^2 \rightarrow R^3, PN(x',y') = \vec{p}(x',y'). \quad (Eq. 7)$$

wherein x' and y' are coordinates of a second coordinate system. The pixel array is aligned with an x' axis and a y' axis of a second coordinate system.

Alternatively, a different polarization normal map $PN_2$ may be considered, wherein the second surface normals are projected onto the image plane 16 of the pixel array:

$$PN_2 = Z^2 \rightarrow R^2, \quad (Eq. 8)$$

$$PN_2(x', y') = P \cdot \vec{p}(x', y') = \begin{bmatrix} f_{x'} & 0 & c_{x'} \\ 0 & f_{y'} & c_{y'} \\ 0 & 0 & 1 \end{bmatrix} \cdot \vec{p}(x', y'),$$

with coordinates of a focal length $f_{x'}$, $f_{y'}$ of the camera 34, and coordinates of a projection center $c_{x'}$ and $c_{y'}$.

Figure 5:
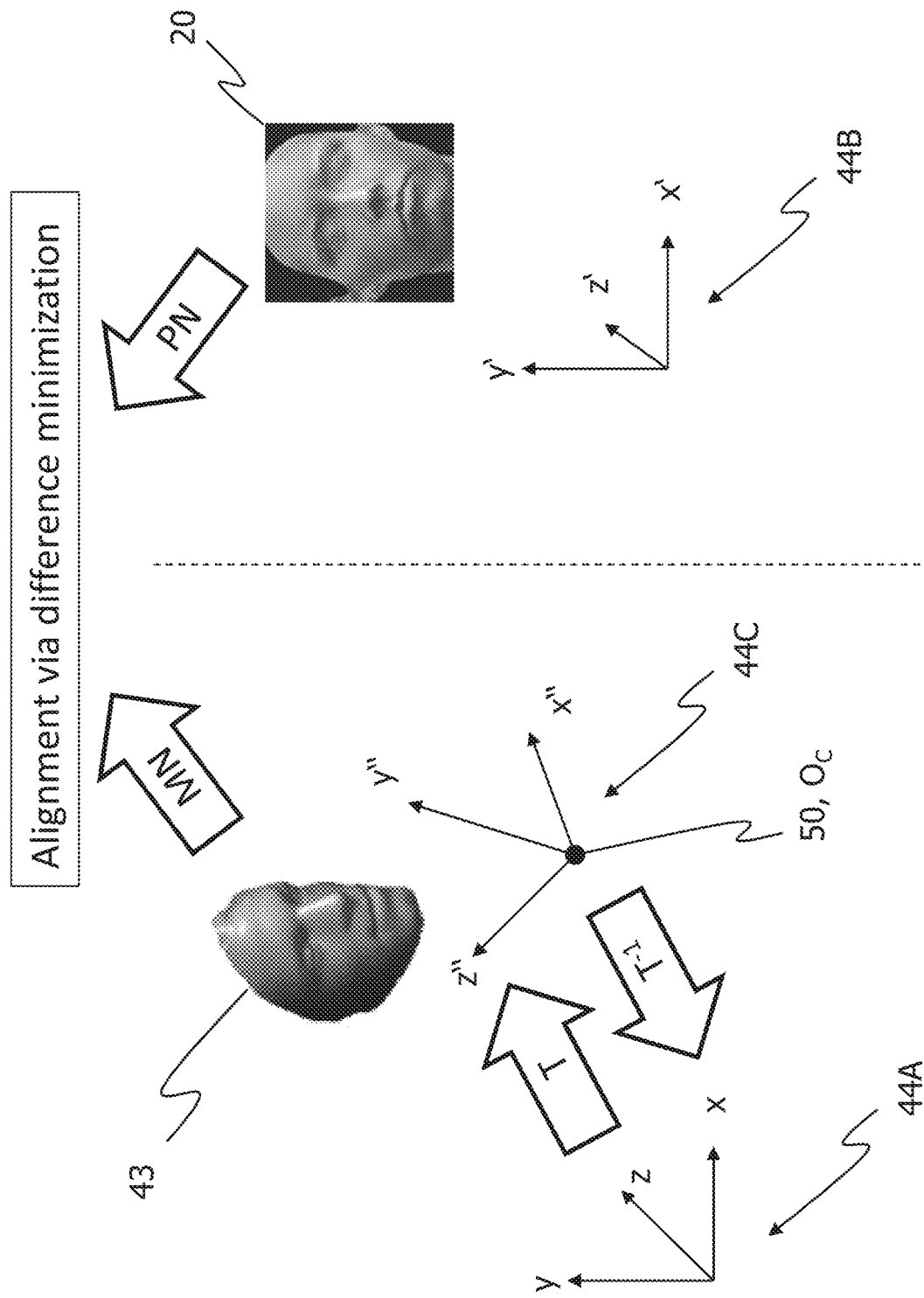
FIG. 5 shows an embodiment of an alignment procedure of first surface normals and second surface normals.

The method 60 further comprises a step 66 of aligning the first surface normals with the second surface normals. FIG. 5 shows an alignment procedure of the first surface normals and the second surface normals.

The three dimensional image data 43 identifies spatial points in the first coordinate system 44A (with coordinates x, y and z). The first coordinate system 44A may, for example, be a coordinate system used during a CT scan or for designing a CAD drawing of a surgical object. The processor 36 is configured to assign each first surface normal a coordinate in the first coordinate system 44A. Areas of the surgical object other than the surface may also be assigned coordinates. For example, spatial points of non-exposed organs of the patient 40, which are therefore not part of the surface captured by the camera 34, are assigned coordinates in the first coordinate system 44A.

The second coordinate system 44B (with coordinates x', y' and z'), on the other hand, is arranged relative to the camera system 32. One possible way to arrange the second coordinate system 44B is to align it with the view point of the camera 34. For example, the origin of the second coordinate system 44B may be placed in the center of the image plane of the camera 34, wherein one of its axes (e.g., the z'-axis) is aligned with the viewing direction of the camera. One advantage of such an orientation is that the image plane and pixel array of the camera 34 extend parallel to the x'-y'-plane of the second coordinate system 44B, which allows assignment of second surface normals of the normal map PN to only the x' and y' axis.

The first surface normals are assigned to three dimensional data 43, wherein the second surface normals are in form of a normal map PN generated from the viewpoint of the camera 34. In order to align the first surface normals with the second surface normals, the first surface normals need to be transformed into a model normal map MN that allows assignment to the polarization normal map PN of the second coordinate system 44B.

For this purpose, a virtual view point 50 is introduced that simulates the view of the camera 34 in the first coordinate system 44A. The model normal map MN is calculated from the virtual view point 50. Such a virtual view point has a viewing direction and a virtual image plane perpendicular thereto. Therefore, one way to implement such a virtual view point 50 is in form of an intermediate third coordinate system 44C (with coordinates x", y" and z") arranged in the first coordinate system 44A. The virtual viewpoint 50 is in a coordinate origin $O_C$ of the third coordinate system 44C, which is to be aligned with a second coordinate system 44B.

Initially, the position and orientation of the third coordinate system 44C are unknown and will be determined during the alignment procedure. Since the alignment procedure requires a comparison between the two normal maps PN and MN and therefore the calculation of a model normal map MN, an initial position of the third coordinate system 44C is arbitrarily selected. The initial position may be, for example, the origin of the first coordinate system 44A, a position of a previous alignment (performed during a previous surgery), an average position of previous alignments or a position selected by the user.

The processor 36 is configured to calculate the model normal map MN of the first surface normals from the virtual view point 50. The model normal map MN is structured like the polarization normal map NP, wherein integer coordinates x", y"∈Z are assigned to normal vectors:

$$MN: Z^2 \rightarrow R^3, MN(x'',y'') = \vec{m}(x'',y'') \qquad (Eq. 9)$$

During alignment, the second and third coordinate system 44B, 44C is to be aligned in such a way that the x and y axis of the second and third coordinate system 44B, 44C align, i.e. x'=x" and y'=y". The model normal map MN may have the same size and side ratios as the polarization normal map PN in order to allow a one-to-one assignment of vectors of both normal maps.

The processor 36 has access to parameters of the camera system 32 that are indicative of a spatial position or optical properties of the camera 34. Such a parameter may be a spatial relation between the camera 34 and the surgical object 40, 42 or other surgical elements such as a surgical bed, the floor or a reference marker. The processor 36 may also determine the spatial relation relative to the surgical object 40, 42 via optical properties of the camera 34, such as focal length or distortion. Since the processor 36 is configured to calculate the spatial relation of the camera 34 relative to the surgical object, the distance between the camera 34 and the surgical object can be calculated. Consequently, the processor 36 is configured to use the same distance between the virtual view point 50 and the surgical object in the three dimensional data 43 as the distance determined between the camera 34 and the surgical object 40, 42.

The processor 36 is configured to align the first surface normals with the second surface normals. To this end, the processor 36 is configured to successively reposition and reorient the virtual view point 50 inside the first coordinate system 44A in such a way that a difference between the model normal map MN (determined for the corresponding virtual view point 50) and the polarization normal map PN is minimized.

The difference between the normal maps may be defined as a sum of differences between first surface normals and second surface normals. In particular, a difference d between two surface normals may be defined as $$d(x',y') = \|\vec{p}(x',y') - (x'',y'')\|^2 \qquad (Eq. 10)$$

Alternatively, the difference may be calculated between projections of the normals onto the image plane with a projection matrix, such as the one defined in equation (8):

$$d(x',y') = \|P \cdot \vec{p}(x',y') - P \cdot \vec{m}(x'',y'')\|^2 \qquad (Eq. 11)$$

With a difference between a first and a second surface normal defined, one example of a difference D to be minimized may be a sum of such differences d:

$$D = \sum_W \sum_V d(x',y') = \sum_W \sum_V \|\vec{p}(x',y') - \vec{m}(x'',y'')\|^2, \qquad (Eq. 12)$$

wherein W and V are parameters that define a set of surface normals to be compared. The set of surface normals may be defined as a section of the pixel array (e.g., a rectangle), a set of normals that are associated with a predefined colour value of the pixel (such as a skin colour), or a set of normals that fulfil a predefined polarization criteria (see further below). Alternatively, the entire set of surface normals may be selected. In this case, W and V span along the entire rows and columns of the pixel array.

The processor 36 is configured to determine, whether the model normal map MN and the polarization normal map PN are sufficiently aligned. An example criterion for the alignment is a predetermined threshold for the difference D. The processor 36 may be configured to determine that the alignment is insufficient of the difference D is above the predetermined threshold. The predetermined threshold may be set by the user, in order to adjust the accuracy of the alignment. The predetermined threshold may also be dependent on the surface curvature of the surgical object. Alignment of a round surface (such as a head of the patient) may require a lower threshold than alignment of a flat surface (such as a stomach area of the patient). Other examples for alignment criteria are a predetermined amount of iteration steps and/or a minimized difference D inside of boundary conditions. A minimized difference D inside of boundary conditions may be defined as the lowest difference determined for a predetermined spatial and angular range or for a predetermined amount of iteration steps.

If the processor 36 determines that the alignment is insufficient, the processor 36 is configured to determine a new position and orientation (from here on defined as "pose") of the virtual view point 50. The new virtual view point 50 may be determined in different ways. The processor 36 may be configured to set the new virtual view point 50 by changing the pose by a predetermined offset. Alternatively, the processor 36 may be configured to determine the offset of the new virtual view point 50 based on a difference D determined for previous virtual view points 50. If, for example, changing the position of the virtual view point 50 gradually increases the difference D, the processor 36 may be configured to change the position in an opposite direction or change the orientation of the virtual view point 50 instead. Alternatively, the processor 36 may be configured to determine the difference D for a first set of multiple poses and determine a second set of poses in the proximity of a pose of the first set of poses that yields the lowest difference D.

The processor 36 is configured to calculate a new model normal map MN at the new pose of the virtual view point 50. If the above mentioned alignment criterion for the new virtual new point 50 is not met, a new pose of the virtual view point 50 is determined as explained above. The calculation of the difference D and the determining of a new pose of the virtual view point 50 are iteratively repeated until the alignment criterion is met. A virtual view point 50 that meets the alignment criteria is defined as an aligned virtual view point 50.

It should be noted that for the purpose of the alignment, the ambiguity of the azimuth angle φ does not need to be resolved. While surface reconstruction usually requires resolving the azimuth ambiguity, experience has been shown that the azimuth ambiguity does not have a significant effect on the alignment procedure.

With the first and second surface normals being aligned, a transformation between the different coordinate systems may be determined. As explained above, the view point 50 is correlated with the third coordinate system 44C. Once the alignment criterion is met, the third coordinate system 44C is arranged at and oriented according to the image plane of the aligned virtual view point 50. The processor 36 is configured to determine a transformation T (such as a rotation and/or translation matrix) that translates and rotates the first coordinate system 44A onto the third coordinate system 44C.

The resulting transformation is a coordinate transformation between the first coordinate system 44A and the third coordinate system 44C. For example, applying the transformation T onto the coordinates of the virtual viewpoint 50 in the first coordinate system 44A will result in the coordinates (0, 0, 0), because in the third coordinate system 44C the virtual view point is in the origin $O_C$ of the third coordinate system 44C. Therefore, $$T(\vec{r}_{virtualviewpoint}) = \vec{0}", \quad (Eq. 14)$$

wherein $\vec{0}"$ is the position of the origin in coordinates of the third coordinate system 44C.

The processor 36 is configured to determine in inverse transformation $T^{-1}$, wherein $$T \cdot T^{-1} = 1. \quad (Eq. 15)$$

Consequently, the inverse transformation $T^{-1}$ transforms coordinates of the third coordinate system 44C into coordinates of the first coordinate system 44A. Using the same point as above, applying the inverse transformation $T^{-1}$ onto the origin $O_C$ of the third coordinate system 44C results in the coordinates of the virtual view point inside the first coordinate system 44A:

$$T^{-1}(\vec{0}") = \vec{r}_{virtualviewpoint}. \quad (Eq. 16)$$

The transformations T and $T^{-1}$ allow calculation of point positions that are known in one coordinate system into another coordinate system.

Since the aligned virtual view point 50 has the same spatial relation to the surgical objects 40, 42 as the camera 34, the transformations T and $T^{-1}$ are also coordinate transformations between the first coordinate system 44A and the second coordinate system 44B.

To give an example, the first coordinate system 44A contains three dimensional image data 43, such as positions of skin surfaces, bones and organs of the patient, but is not aligned with the patient during surgery. In the second coordination system 44B, on the other hand, the position and orientation of the patient during surgery is known, but it only contains information about the surface in form of surface normals. After aligning the second and third coordination system 44B, 44C, the three dimensional image data 43 can be transferred to the second coordinate system 44B via the transformation T. A CT scan may, for example, contain the coordinates $\vec{r}^{tumour}$ of a tumour in the first coordination system 44A. The position of the tumour $\vec{r}_{tumour}$ in the second coordination system 44B (i.e., the coordination system of the camera 34) can be calculated with equation (17):

$$\vec{r}'_{tumour} = T(\vec{r}_{tumour}) \quad (Eq. 17)$$

The processor 36 may be configured to superimpose an image of the tumour and of the images recorded with the camera 34 and send the superimposed image to a monitor (not shown) for the surgeon to see.

The same principle applies to other surgical objects, such as a surgical instrument 42. It is also possible to register a plurality of surgical objects. As shown in FIG. 3, two surgical objects in form of a patient 40 and a surgical instrument 42 are in the field of view of the camera 34. Therefore, both surgical objects 40, 42 have the same second coordinate system 44B. However, the first coordinate systems 44A are different, for example because the three dimensional image 43 data of the patient 40 is a CT scan, whereas the three dimensional image data 43 of the surgical instrument 42 is a CAD data set.

Consequently, both surgical objects (patient 40 and surgical instrument 42) need to be aligned separately, which results in two different transformations $T_{patient}$ and $T_{instrument}$. Once these two transformations are determined, three-dimensional coordinates of both surgical objects 40, 42 can each be transformed into the common second coordinate system 44B. The processor 36 can therefore calculate a spatial relation between the patient 40 and the surgical instrument 42. The processor 36 may be configured to superimpose the three dimensional data 43 of the patient 40 and the surgical instrument 42 into a common image for presentation to the surgeon. The image may further comprise the image recorded by the camera 34. In this way, the navigation system 30 helps the surgeon navigate the surgical instrument 42 (e.g. its tip) relative to the patient 42.

The camera system 32 shown in FIG. 3 comprises a camera 34 with a rotatable polarization filter 26. The rotatable polarizer 26 may be realised in different ways. It may comprise a glass or polymer sheet with a polarizing layer, wherein the polarization angle can be adjusted by rotating the glass or polymer sheet (e.g., by means of an actuator such as an electric motor or piezo-elements). Alternatively or additionally, the polarizer may comprise optically active elements, such as liquid crystal cells. Optically active elements can change the polarization angle faster and more energy efficient than a mechanically driven polarization filter.

The camera system 32 may be configured to capture images with a plurality of cameras 34 each with its own polarization filter. Such a surgical navigation system 30 is shown in FIG. 5. The camera system 32 comprises three cameras 34A, 34B, 34C, each with a polarization filters 26A, 26B, 26C. The polarization filters 26A, 26B, 26C have different and fixed polarization angles and therefore allow the cameras 34A, 34B, 34C to capture images of a same object with different polarization angles. In such an embodiment, no mechanism for rotating a polarization filter is necessary.

The aforementioned technique of alignment allows registering of a surgical object, which involves alignment of the coordinate system of the camera with coordinate systems of three dimensional data.

After registering the surgical object, the object may be tracked by identifying the pose for consecutive time slots (e.g., video frames). Given enough computing capacities, the tracking can also be performed through the above mentioned surgical navigation (i.e., via surface-from-polarization). It should be noted that the computational costs of determining the pose for each consecutive time slot is usually lower than for the initial registration. During the registration, the aligned virtual view point 50 may need to be searched on the entire sphere around the surgical object. However, once the aligned virtual view point 50 is determined, the new virtual view point 50 for the consecutive time slot is expected to be located close to the previous virtual view point 50, which reduces the angular range for searching the new virtual view point 50.

A less computationally expensive approach is to perform the registration via surface-from-polarization as explained above and then continue tracking through other means such as stereo photogrammetry or electromagnetic tracking. Examples of such arrangements are shown in FIGS. 7A-7D.

FIG. 7A shows a surgical navigation system 30 with a rotatable polarizing filter 26 in combination with a stereo camera 45 with two cameras 47A, 47B. The dashed lines indicate a camera lens behind the polarizing filter 26.

The surgical navigation system 30 allows registration, i.e. alignment of the first surface normals and second surface normals of surgical objects. Once the surgical objects are registered, the stereo camera 45 tracks movement of the surgical objects. To this end, markers may be attached to the surgical objects to be tracked by the stereo camera 45. Furthermore, a spatial relation between the camera system 32 and the stereo camera 45 is known. The processor 36 (or another processor, such as a processor of the stereo camera) can calculate a coordinate transformation between the camera system 32 and the stereo camera 45 from the known spatial relation.

Figure 6:
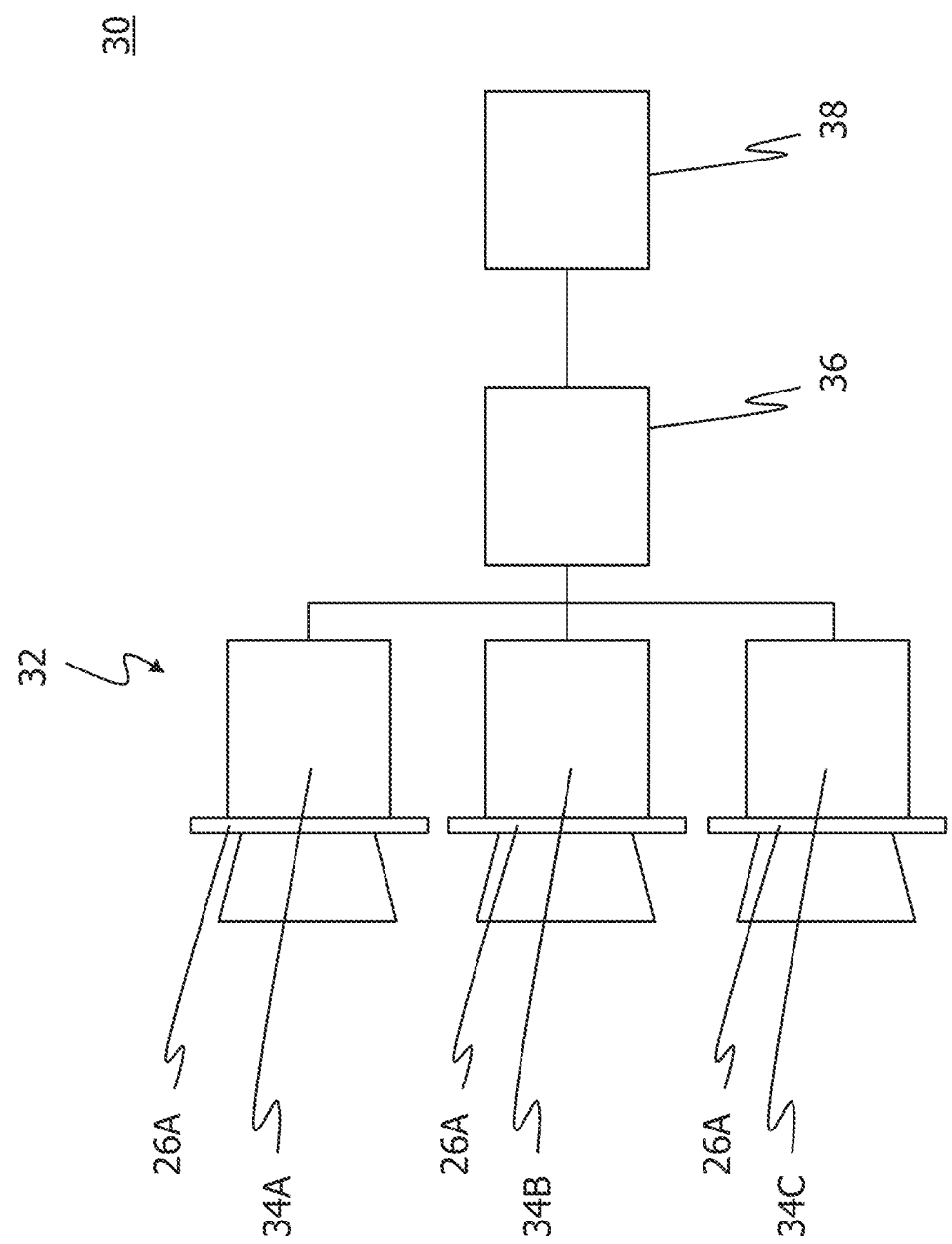
FIG. 6 shows an embodiment of a surgical navigation system comprising a camera system with a plurality of cameras.

FIG. 7B shows a stereo camera 45, wherein one of the two cameras 47A, 47B comprises a rotatable polarizing filter 26. The stereo camera 45 also comprises other elements such as the processor and storage medium (not shown) that enable registering surgical objects as explained above. After registration, the camera 47B with the polarizing filter 26 can be used in combination with the other camera 47A in order to perform tracking of the surgical objects in a stereo photogrammetry mode. Compared to the scenario of FIG. 6A, the setup requires one camera less and has a fixed spatial relation between the cameras, which reduces calibration complexity.

FIG. 7C shows a stereo camera 45, wherein both cameras 47A, 47B comprise a rotatable polarizing filter 26. Either camera can be used for registration. Additionally, each camera 47A, 47B can be used to register a different surgical object.

FIG. 7D shows an apparatus 46 for electromagnetic tracking in combination with a surgical navigation system 30. The apparatus 46 generates an electromagnetic field that couples with surgical objects. The electromagnetic field may couple with an electrically conductive coil that is attached to the surgical object. Through the coupling the apparatus can track the surgical object. The initial registration is performed by the surgical navigation system 30, whereas the tracking afterwards is performed by the apparatus 46 for electromagnetic tracking.

Since the surgical navigation system 30 is capable of determining a degree of polarization, further information can be gained from the captured images. The degree of polarization is indicative of the reflecting material of the surface. Reflective materials such as metals or liquid surfaces tend to reflect the light specularly, which results in a higher degree of polarization. On the other hand, when a surface reflects predominantly diffusively, the degree of polarization is comparably lower. These different reflective behaviours enable distinguishing different types of surfaces.

As explained above, for each pixel of the camera 34, a (second) surface normal is determined, which comprises determining the degree of polarization. Therefore, for each pixel of the camera 34, the degree of polarization can be recorded. The processor 36 may be configured to determine if a surgical object is of a first type if a degree of polarization determined for a second surface normal is lower than a first threshold. The first type surgical object may be the patient or a surgical instrument with a non-metallic casing. Such surgical objects reflect light predominately diffusively, which results in a low degree of polarization. When the processor 36 determines that the degree of polarization is below the first threshold, it identifies the surgical object as the first type (e.g., the patient).

The processor 36 may further be configured to determine that the surgical object is of a second type if a degree of polarization determined for the second surface normal is higher than a second threshold. The second type surgical object may be a surgical instrument (e.g., with a metal casing). Such a surgical instrument reflects predominately specularly and therefore with a high degree of polarization. The processor 36 is configured to detect that the reflected light is above the second threshold and determines that the corresponding surface normal can be assigned to the second type surgical instrument. The first and the second threshold may be identical.

Similarly, the processor 36 may be configured to determine whether a surface is covered by a liquid or not. During surgery, exposed surgical objects such as bones may be covered by liquids such as water, blood or disinfectants. Such surfaces reflect light predominantly specularly, which results in a high degree of polarization. Therefore, the processor 36 may determine if a surface is covered by a liquid, when the degree of polarization is above a predetermined threshold. The processor 36 may have a predetermined threshold for different types of liquid.

The degree of polarization can also indicate whether a surface reflects or emits light. A light source usually emits unpolarized light, wherein reflected light tends to be at least partially polarized. Therefore, the processor 36 may be configured to determine whether a surface emits light if a degree of polarization is below a pre-determined threshold. Distinguishing between light emission and light reflection can be useful to distinguish between a tracker that operates with an active light source from a reflecting surface (e.g., a bone covered with blood). For registering the tracker, the processor 36 may ignore light spots with a degree of polarization above the threshold, which allows the processor 36 to isolate light sources of the tracker in the captured image.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

In this application, including the definitions below, the terms processor, module, and controller may be replaced with the term circuit. The terms processor, module, controller, and circuit may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash drive, a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and/or flow diagrams elements described above may serve as software specifications, which can be translated into the computer applications or programs by the routine work of a skilled technician or programmer.

The computer applications or programs include processor-executable instructions that are stored on at least one non-transitory computer-readable medium. The computer application or programs may also include or rely on stored data. The computer application or programs may encompass a basic input/output system (BIOS) that interacts with hardware of the special purpose computer, device drivers that interact with particular devices of the special purpose computer, one or more operating systems, user applications, background services, background applications, etc.

The computer applications or programs may, for example purposes only, include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. The source code may be written using syntax from any suitable language.

What is claimed is:

1. A surgical navigation system comprising
a camera system comprising at least one camera, wherein the camera system is capable of capturing images of light that is filtered through at least three different polarization angles;
a processor having access to three dimensional image data of a surgical object and being configured to:
determine first surface normals from the three dimensional image data of the surgical object;
determine second surface normals of the surgical object from at least three images captured of the surgical object by the camera system under different polarization angles; and
align the first surface normals with the second surface normals.

2. The surgical navigation system according to claim 1, wherein the processor is configured to align the second surface normals with the first surface normals to determine a transformation of coordinates of the first surface normals in a first coordinate system into a second coordinate system of the second surface normals.

3. The surgical navigation system according to claim 2, wherein the transformation is determined by a minimization of a sum of differences between the first surface normals and the second surface normals.

4. The surgical navigation system according to claim 3, wherein the processor is configured to calculate a difference between two surface normals as the magnitude of a vector difference between the two surface normals.

5. The surgical navigation system according to claim 2, wherein the transformation is determined by a minimization of a sum of differences between projections of the first surface normals and the second surface normals onto an image plane of the camera system.

6. The surgical navigation system according to claim 1, wherein the processor is configured to differentiate if the surgical object is of a first type or a second type based on a degree of polarization determined for the second surface normals of the surgical object.

7. The surgical navigation system according to claim 6, wherein the processor is configured to at least one of determine that the surgical object is of the first type if a degree of polarization determined for the second surface normals of the surgical object is lower than a first threshold and to determine that the surgical object is of the second type if a degree of polarization determined for the second surface normals of the surgical object is higher than a second threshold.

8. The surgical navigation system according to claim 1, wherein the processor is configured to differentiate if a second surface normal of the second surface normals is pertaining to a surface or surface region covered by liquid based on a degree of polarization determined for the second surface normal of the second surface normals.

9. The surgical navigation system according to claim 8, wherein the processor is configured to determine that the second surface normal of the second surface normals is pertaining to a surface or surface region covered by liquid if the degree of polarization determined for the second surface normal of the second surface normals is above a third threshold.

10. The surgical navigation system according to claim 1, wherein the processor is configured to differentiate if a second surface normal of the second surface normals is pertaining to a surface emitting or reflecting light based on a degree of polarization determined for the second surface normal of the second surface normals.

11. The surgical navigation system according to claim 10, wherein the processor is configured to at least one of determine that the second surface normal of the second surface normals is pertaining to a light emitting surface if the degree of polarization determined for the second surface normal of the second normals is below a fourth threshold and to determine that the second surface normal of the second surface normals is pertaining to a light reflecting surface if the degree of polarization determined for the second surface normal of the second normals is above a fifth threshold.

12. The surgical navigation system according to claim 1, wherein the processor is configured to determine the second surface normals from the at least three images by fitting a light intensity of pixels of the captured images to a sinusoid model that describes a magnitude of a light beam having a light beam polarization angle passing through a polarization filter.

13. The surgical navigation system according to claim 1, wherein the processor is configured to determine the second surface normals from the at least three images by using a Fresnel equation.

14. The surgical navigation system according to claim 1, wherein the processor is configured to determine or have access to at least one parameter of at least one camera of the camera system that is indicative of at least one of a spatial position and optical properties of the at least one camera of the camera system.

15. The surgical navigation system according to claim 1, wherein the processor is further configured to track a second type surgical object relative to a first type surgical object by calculating a position and orientation of the second type surgical object relative to the first type surgical object.

16. The surgical navigation system according to claim 15, wherein the first type surgical object is a patient or a part thereof and the second type surgical object is a surgical instrument.

17. The surgical navigation system according to claim 1, wherein the three dimensional data was previously acquired from at least one of an unknown position and an unknown viewing angle.

18. The surgical navigation system according to claim 1, wherein the camera system comprises optically active elements configured to rotate a polarization angle of polarized light entering the camera system.

19. A method for operating a surgical navigation system, the surgical navigation system comprising a camera system comprising at least one camera, wherein the camera system is capable of capturing images of light that is filtered through at least three different polarization angles, and having access to three dimensional image data of a surgical object; the method comprising:
   determining first surface normals of the surgical object from the three dimensional image data;
   determining second surface normals of the surgical object from at least three images captured by the camera system of the surgical object under different polarization angles; and
   aligning the first surface normals with the second surface normals.

20. A non-transitory computer-readable medium that stores programming instructions for execution, that when executed on at least one processor, cause the at least one processor to carry out a method comprising:
   determining first surface normals of a surgical object from three dimensional image data;
   determining second surface normals of a surgical object from at least three images captured by a camera system of the surgical object under different polarization angles; and
   aligning the first surface normals with the second surface normals.

* * * * *